United States Patent
Alejandro (10) Patent No.: US 9,351,823 B2
(45) Date of Patent: May 31, 2016

(54) THERAPEUTIC BREAST IMPLANTS

(76) Inventor: Kathia Alejandro, Guaynabo, PR (US)

( * ) Notice: Subject to any disclaimer, the term of this patent is extended or adjusted under 35 U.S.C. 154(b) by 897 days.

(21) Appl. No.: 12/945,648

(22) Filed: Nov. 12, 2010

(65) Prior Publication Data

US 2012/0123535 A1     May 17, 2012

(51) Int. Cl.
*A61F 2/12*              (2006.01)

(52) U.S. Cl.
CPC ........................................ *A61F 2/12* (2013.01)

(58) Field of Classification Search
CPC .......... A61F 2002/30586; A61F 2/441; A61F 2/442; A61F 2/12
USPC ................ 604/131–133; 623/8, 14.12, 17.12; 606/192
See application file for complete search history.

(56) References Cited

U.S. PATENT DOCUMENTS

| | | | | |
|---|---|---|---|---|
| 3,683,424 | A | * | 8/1972 | Pangman ........................... 623/8 |
| 4,264,990 | A | * | 5/1981 | Hamas ............................... 623/8 |
| 4,428,082 | A | * | 1/1984 | Naficy ............................... 623/8 |
| 2003/0036803 | A1 | * | 2/2003 | McGhan ........................... 623/8 |
| 2007/0276377 | A1 | * | 11/2007 | Yundt .............................. 606/61 |
| 2010/0137985 | A1 | * | 6/2010 | Purkait ............................... 623/8 |
| 2011/0208302 | A1 | * | 8/2011 | Glicksman ........................ 623/8 |

FOREIGN PATENT DOCUMENTS

WO     WO 2009097347 A1 *   8/2009   ................ A61F 2/12

* cited by examiner

*Primary Examiner* — Brian Pellegrino
(74) *Attorney, Agent, or Firm* — Eugenio J. Torres-Oyola; Victor Rodriguez-Reyes; Ferraiuoli LLC (57) ABSTRACT

A breast implant and process to optimize the treatment of breast cancer patients that offers more effective alternatives in breast reconstruction and simultaneously administers regional therapies in order to minimize the possibility of local recurrences. The breast implant comprises an inner porous core contained by an elastic holding layer with a system of tubes and conducts within it covered with biodegradable chemotherapeutic and attaching layers.

11 Claims, 7 Drawing Sheets

THERAPEUTIC BREAST IMPLANTS

STATEMENT REGARDING FEDERALLY SPONSORED RESEARCH AND DEVELOPMENT

N/A

RELATED APPLICATIONS

N/A

BACKGROUND OF THE INVENTION

1. Field of the Invention

The present invention is generally directed to management of breast cancer. More particularly, the present invention relates to a breast implant that optimizes breast reconstruction and local regional treatment after surgical intervention for breast cancer.

2. Discussion of the Background

Studies have demonstrated that a good aesthetic result after breast cancer surgery has a key role in the overall outcome of patients. The psychological consequences of absence or deformity of the breast after surgery can be devastating. In the quest for better patient outcome, breast surgery has evolved to a point in which most of the patients these days do not need complete resection of the breast for the management of their cancer. Partial breast resection is accepted and promoted by medical experts even when radiotherapy is required because it is much better tolerated than total mastectomy. But there are still a lot of patients in which mastectomy, complete resection of the breast, is required as the indicated surgical intervention. Again, the psychological effects for these kinds of surgery are devastating and debilitating.

Reconstructive surgery has been developed to treat deformity and acquired absence of the breast. But the real availability and accessibility of breast reconstructions are limited mostly because of the complexity of breast reconstructive surgery when myocutaneous and free tissue flaps are used. Breast reconstruction with implantable prostheses are more simple and accessible, but less aesthetically favorable. Therefore, a breast implant should be developed to meet requirements in a way that breast implant reconstruction could achieve the same aesthetic results than reconstruction with tissue flaps.

Currently the problem with breast implant reconstruction after mastectomy is that the implants become very noticeable underneath breast skin flaps. First, the implant itself has a very unnatural feeling. Also, the process of encapsulation adds to the situation causing the entire natural drop-like appearance of the breast tissue to be lost and increasing breast stiffness.

Furthermore, if additional local treatment, such as radiotherapy, is needed after surgery, the implant may interfere with its planning and administration. Finally, when implants are used for breast reconstruction in most cases several surgical interventions are required until the desirable volume and shape are achieved.

Presently, the available prostheses devices emerge from the family of implants developed initially for aesthetic purposes. This is a founding problem because the requirements of breast implants to meet the needs after aesthetic breast surgery are very different than those for reconstructive surgery after mastectomy. Some implants, more particularly the ones used for aesthetic breast surgery, have been improved to make them less noticeable after breast reconstruction. However, the main focus in their improvements is the implant filling and not the implant shell or outer surface. The shell serves as a support for the implant filling, however the material used for the implant filling is just one of the factors affecting how the implant feels.

The elasticity of the shell is a characteristic that affects the feeling and look of the breast. For example, if the elasticity of the shell of the implant is less than the elasticity of the skin then you will always feel the implant below the skin flaps.

Another important remark is the body reaction, such as encapsulation to the implant, which makes the implant more noticeable and uncomfortable to the patient. As mentioned before, the shell is the implant's portion closer to the patient's tissue, therefore the coating of the shell affects the mastectomy bed as well the feeling of the implant. Encapsulation is more accentuated after reconstruction, because skin flaps are thinner. The body reaction that leads to implant encapsulation is the same reaction that leads to tissue adhesions surrounding non-biodegradable material which is a foreign body reaction. Whenever the body is incapable of degrading or attacking any given "foreigner", such as prolene and silicone, it will elicit a foreign body reaction where it tries to encapsulate the invader. This reaction creates a very high collagen content pseudomembrane with myofibroblasts that contracts around it. Therefore, there is a need to reduce the encapsulation reaction in order to provide a more natural feeling of the breast implant.

Further, as mentioned before, in order to provide a breast implant that does not just focuses on the aesthetics but also the reconstructive breast cancer surgery certain features can be added to make them more useful for breast reconstruction and local regional therapy. For example, the delivery of a drug for local treatment to the mastectomy bed in order to reduce, control and treat the patient's condition. Therefore, there is a need of a breast implant capable of delivering a drug or serving for post-mastectomy local treatment after breast reconstructive surgery.

While some breast implants, such as previous breast implant directed to reconstruction surgery, have proven to assist with post-mastectomy regional treatment and reconstruction, still further improvements would be desirable. In general, it would be desirable to provide a breast implant improving the shell performance with regards to reactions with the patient's tissue surrounding the implant, while maintaining a natural look and sensation of the implant. The ideal implant would be one that you can use for breast reconstruction immediately after mastectomy, allows for local regional treatment after surgery, does not encapsulate and feels like a normal breast. In addition, it would permit inflation or deflation at any time after surgery. After insertion during mastectomy no further operating room intervention would be needed. The purpose of this invention is to fulfill those requirements.

Any shortcoming mentioned above is not intended to be exhaustive, but rather is among many that tends to impair the effectiveness of previously known techniques for breast reconstruction; however, shortcomings mentioned here are sufficient to demonstrate that the methodologies appearing in the art have not been satisfactory and that a significant need exists for the techniques described and claimed in this disclosure.

SUMMARY OF THE INVENTION

The present invention is generally related to a breast implant for breast reconstruction surgery, wherein said breast implant assisting with post-mastectomy local regional treatment while providing a natural look and sensation. The present breast implant reconstruction achieves the same aesthetic results than reconstruction with tissue flaps. The breast implant disclosed herein comprises from inner to outer: a porous core and filling fluid held by a first layer made of elastic material containing a system of tubes for local therapy, a second layer with biodegradable chemotherapeutic properties, and third and outer layer consisting of a biodegradable mesh for further covering and attaching purposes.

In a first embodiment of the present invention, the implant has an inner core that comprises a cohesive elastic material with interconnected pores to allow inflation/deflation of the implant with filling fluid. The cohesive elastic material adds substance to the implant for a more natural feeling, while the pores and/or interconnected spaces allow the implant to be inflated or deflated to a desirable volume.

Another aspect of the present invention consists of a first layer of an elastic material to hold the inner core and filling fluid of the implant. This first layer will have a system of tubes for post-mastectomy local therapy. The tubes or channels are organized in a mesh-like arrangement for the administration of brachytherapy. The channels are sectioned in particular areas as brachytherapy could be preferentially administered trough specific sections of the implant and not only at the posterior wall of the prostheses. The whole mastectomy bed can be treated in this way. A catheter going through the skin and connected to the breast implant will be used for the administration of the therapeutic agent for brachytherapy. The catheter will be pulled out after the therapy is finished. The material used for this layer comprises an elastic low toxicity material, such as silicone. It is the less elastic layer of the overall implant, but will have more elasticity than the average elasticity of the skin. The material used is an opaque material to avoid translucency below the skin flaps.

In addition, this invention will have a second layer that provides local chemotherapy treatment after mastectomy. This layer will coat the first one with a biodegradable substance, such as a vicryl mesh, with drug eluting properties. The drug to be eluted is proposed to be a chemotherapeutic agent for the management of breast cancer, for example paclitaxel. This second layer minimizes the possibility of encapsulation simultaneously serving for therapeutic purposes.

In addition, a third layer is added to provide an attachment for the implant. This third layer provides a biodegradable coating extending 2-3 cm away from the implant borders. For example, like a small mesh extension all around its border that will allow fixation as needed to any point in the dissection bed made up for the implant.

An additional feature of this invention is to provide barely noticeable permanent ports for administrating the therapeutic agent and for inflating and deflating the implant anytime after insertion. Small permanent ports are placed at the posterior aspect of the implant, for deflation and inflation. It will be accessed by ultrasonic guidance, with the patient placed on the lateral decubitus position. In this position the ports are accessed while it is placed in the posterior aspect of the implant. The ports are angularly oriented, such as in a diagonal configuration so that when the patient is in the lateral decubitus position, it will be perpendicular to the physician performing the procedure, for an adequate approach to the ports. The ultrasonic guidance will permit finding the port in this posterior position. In addition, since the port will be identified by ultrasound guidance a port of a smaller diameter is developed. The posterior position of the ports and smaller size helps to hide the port and make it practically unnoticeable. The port used for brachytherapy will also be accessed with ultrasonic guidance. It will be accessible anytime after mastectomy.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers refer to like elements. The drawings, which are not necessarily to scale, illustratively depict embodiments of the present invention and are not intended to limit the scope of the invention.

DESCRIPTION OF THE PREFERRED EMBODIMENT

Figure 1:
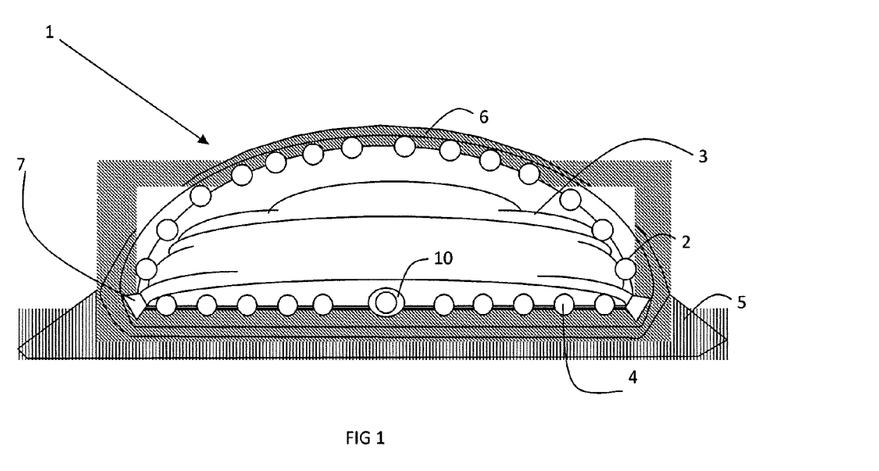
FIG. 1 shows an exemplary breast implant constructed in accordance with the principles of the present invention.
Figure 2A:
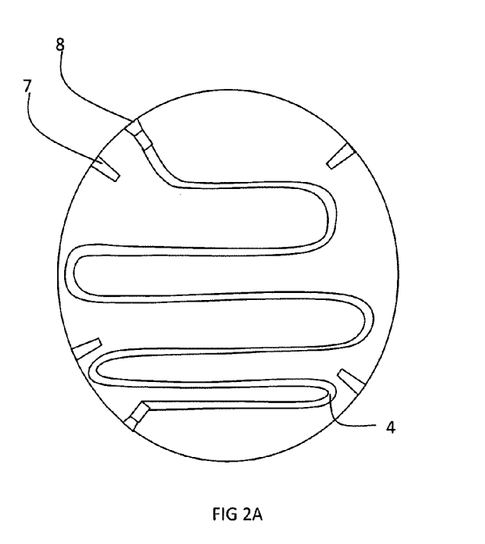
FIGS. 2A through 2B show the inner surface of a breast implant constructed in accordance with the principles of the present invention.
Figure 2B:
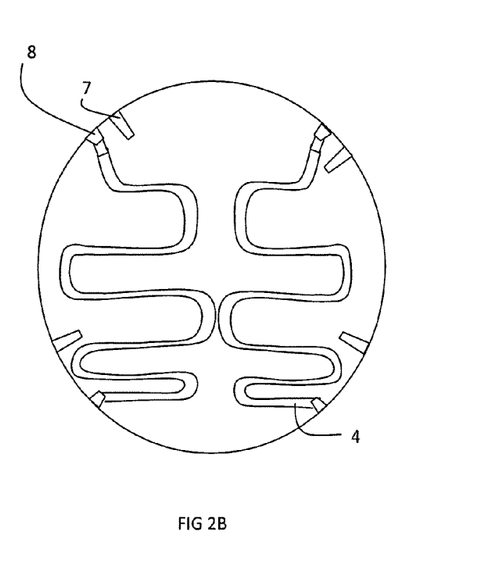

FIG. 1 shows an exemplary breast implant constructed in accordance with the principles of the present invention, wherein the breast implant 1 comprises a breast implant with an inner core 3 and first layer 2, wherein said first layer limits the boundaries of the implant filling. A series of tubes, conducts or channels 4 are positioned on the first layer's 2 inner aspect. Further, a porous core 3 made of a malleable cohesive material having a degree of stiffness to add body comprises a series of interconnected spaces, such as pores spaces, holes or channels, so as to allow inflation of the implant with filling fluid passing through the porous core by means of said interconnected spaces. The filling fluid comprises a selection of a fluid with none or low degree of toxicity towards the human body, such as silicon or saline water. A biodegradable layer 6 which is the second layer of the implant elutes a chemotherapy drug to serve as a regional therapeutic agent and minimize the possibility of encapsulation, said biodegradable layer 6 surrounds the first layer 2, and an attached third layer 5 extend from the boundaries of the biodegradable layer 6. The third layer 5 and biodegradable layer 6 can be integrally made. The third layer may also cover and coat entirely the second layer with the extending mesh for attachment. The first layer 2 is made of a non toxic elastic material. The conduct 4 is placed inside the first layer's inner surface. The first layer holds the inner contents of the implant which are the porous core 3 with filling fluid. The biodegradable layer 6 and extendable attaching layer 5 are located at the outer surface of the first layer; these are the second and third layers as described earlier. Several ports are connected to the first layer 2, wherein at least a first port 7 serves as an access point to fill the breast implant with a filling material such as silicon or saline water. A second port or therapeutic port 10 serves as an access point to the therapeutic or brachytherapy fluid agent.

FIG. 2 through FIG. 8B are directed to the brachytherapy system. The brachytherapy system comprises at least one tube 4 having an input port 8 to provide the therapy fluid. As shown in FIG. 2A the conducts 4 are arranged through the lining of the implant in a pre-determined way in order to cover most of the first layer's inner surface. Furthermore, the system's tube arrangements can be allocated in such way as to particularly select an area or surface to be treated as shown in FIG. 2B, allowing for partial as well as complete post-mastectomy breast brachytherapy treatment.

Figure 3A:
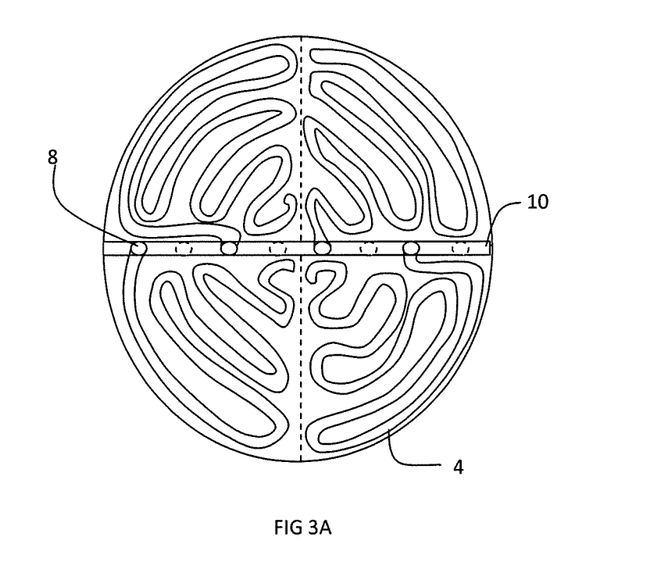
FIGS. 3A through 3B shows a top and side view of a second exemplary breast implant constructed in accordance with the principles of the present invention.
Figure 3B:
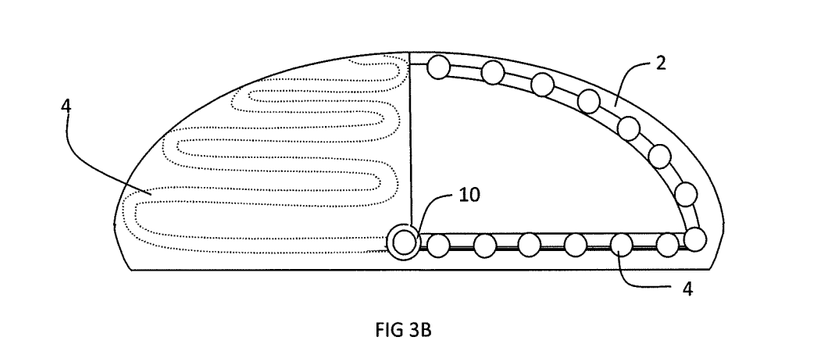

FIG. 3A shows an exemplary breast implant 1 constructed in accordance with the principles of the present invention, wherein the arrangement of tubes 4 is divided in at least eight sections, each section representing a quadrant of the breast implant outer surface. The back part of the breast implant 1 is divided into four quadrants and the front or top part is divided into another four quadrants. Other divisions can be made as desired, for example the retroareolar area that may be partially irradiated after nipple sparing mastectomy. Each quadrant has an input port 8 connected to a main therapeutic port 10 which provides the main access point for supplying the therapy fluid to be used for brachytherapy at each zone or quadrant. In this example, the physician may choose to administer a higher brachytherapy doses to a particular zone of the patient's mastectomy bed. FIG. 3B shows the side view of the present embodiment in accordance with the principles of the present invention.

Figures 4, 5A, 5B, 5C:
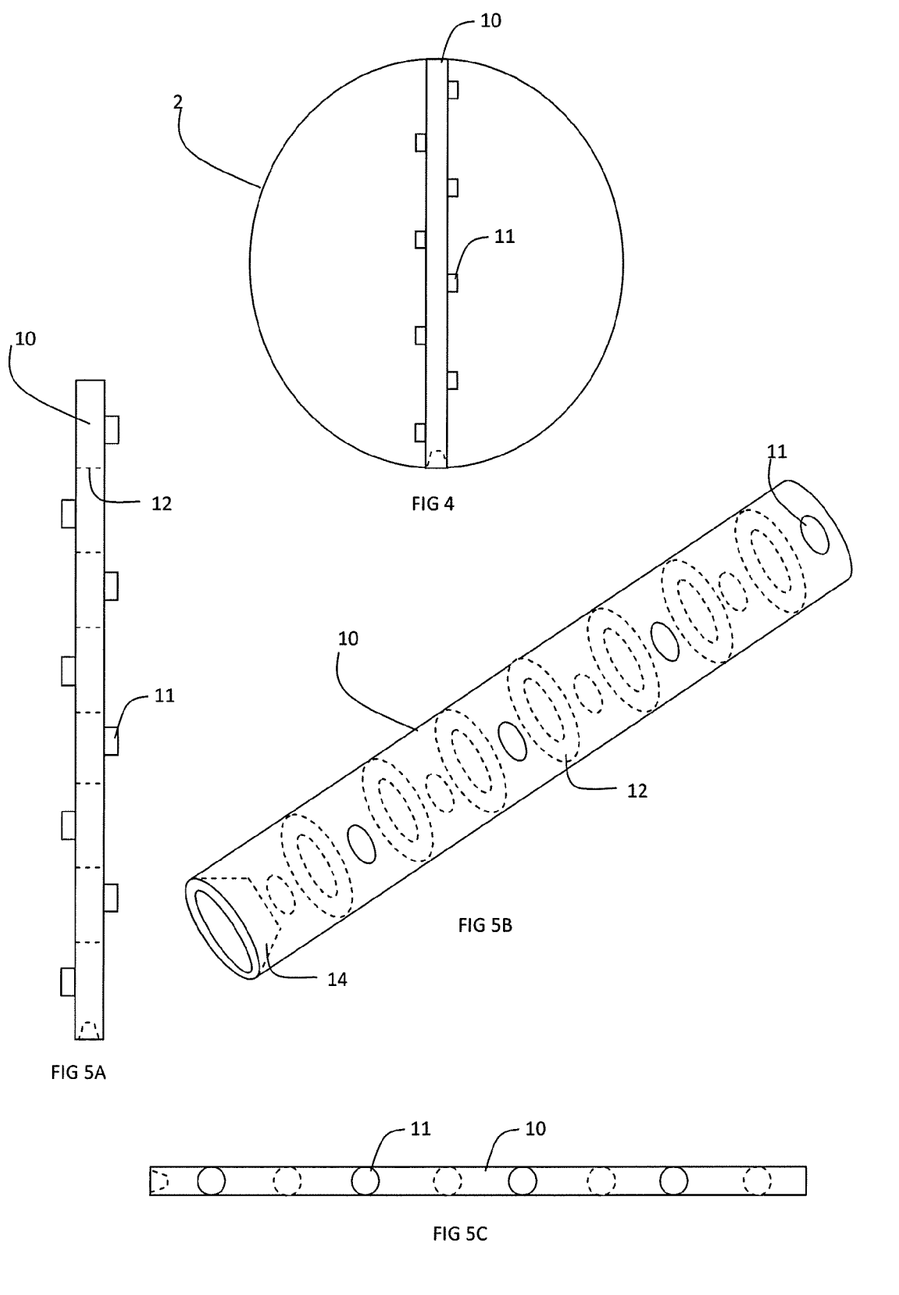
FIG. 4 shows an exemplary breast implant with brachytherapy input port constructed in accordance with the principles of the present invention.
FIGS. 5A through 5C show different views of the brachytherapy input port constructed in accordance with the principles of the present invention.

The therapeutic port 10 of the breast implant 1 divided into several sections which are disclosed in more detail in FIG. 4 through FIG. 5C. FIG. 4 omits all the other elements previously described and presents the back aspect of the inner first layer 2 with the therapeutic port 10. The therapeutic port 10 extends between the boundaries of the first layer 2 at the back of the implant. FIGS. 5A through 5C show in more detail the therapeutic port 10 comprising an elongated body with several openings or inputs 11 serving as connections for conducts 4 on each quadrant. The therapeutic port 10 is divided by soft rings 12 located inside the cylindrical elongated body. The purpose of the rings 12 is to avoid transfer of fluid between sections. For example, if a therapy fluid is to be applied to the first and third quadrant of the implant, the ring 12 avoids the transfer of fluids between the first section, the third section and any other section in between. The therapeutic port 10 has a first funnel-shape input 14 located at a distal end of the elongated body.

Figure 6:
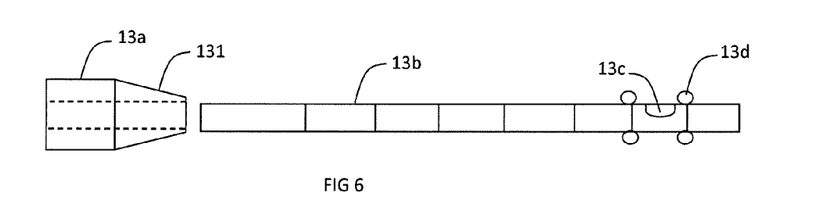
FIG. 6 shows a brachytherapy fluid supplier constructed in accordance with the principles of the present invention.

FIG. 6 shows the brachytherapy fluid supplier 13 wherein the main purpose is to dispense therapeutic fluid into the therapeutic port 10. The brachytherapy fluid supplier 13 comprises an elongated cylindrical body 13b with a diameter smaller than the input port 10, connected to a supplier main body 13a. Said supplier main body 13a has a second funnel-shaped structure 131 configured to fit said first funnel-shaped input 14. Once both funnel shaped elements are positioned in place the brachytherapy fluid supplier 13b is inserted through the input port 10 in the implant. The elongated body 13b comprises an opening at the distal end 13c serving as an output for the therapeutic agent traveling through the elongated body 13b. Further, a set of balloons 13d serving as a sealer surrounds the opening and assist the ring 12 to avoid the transfer of therapeutic fluid between quadrants.

Figure 7A:
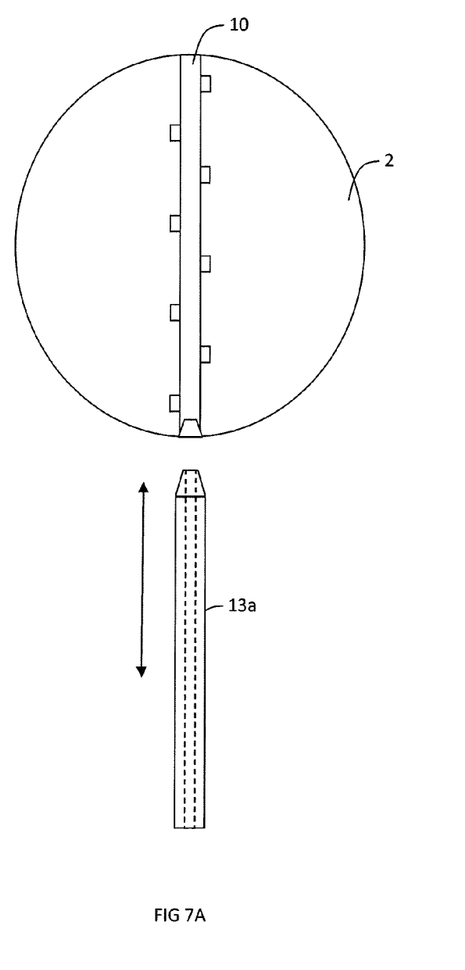
FIGS. 7A through 7B show the insertion process of the brachytherapy or therapeutic fluid agent supplier in the brachytherapy input port in accordance with the principles of the present invention.
Figure 7B:
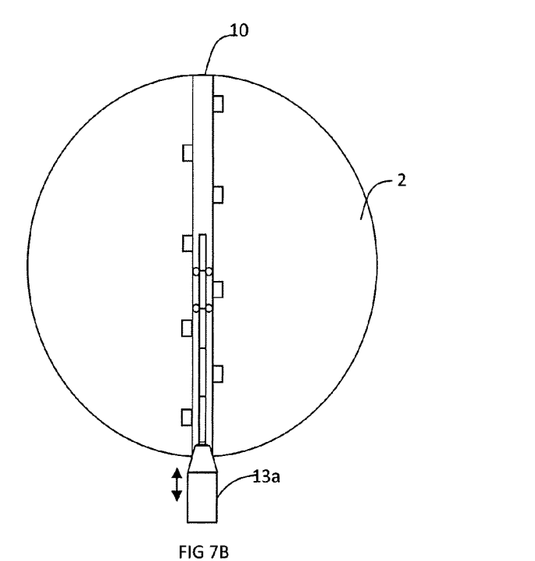
Figure 8A:
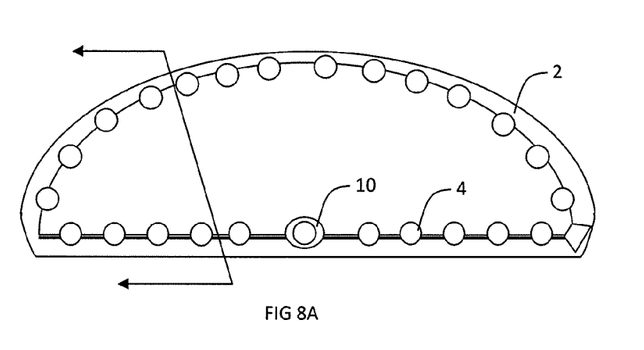
FIGS. 8A through 8B show the brachytherapy conducts in accordance with the principles of the present invention.
Figure 8B:
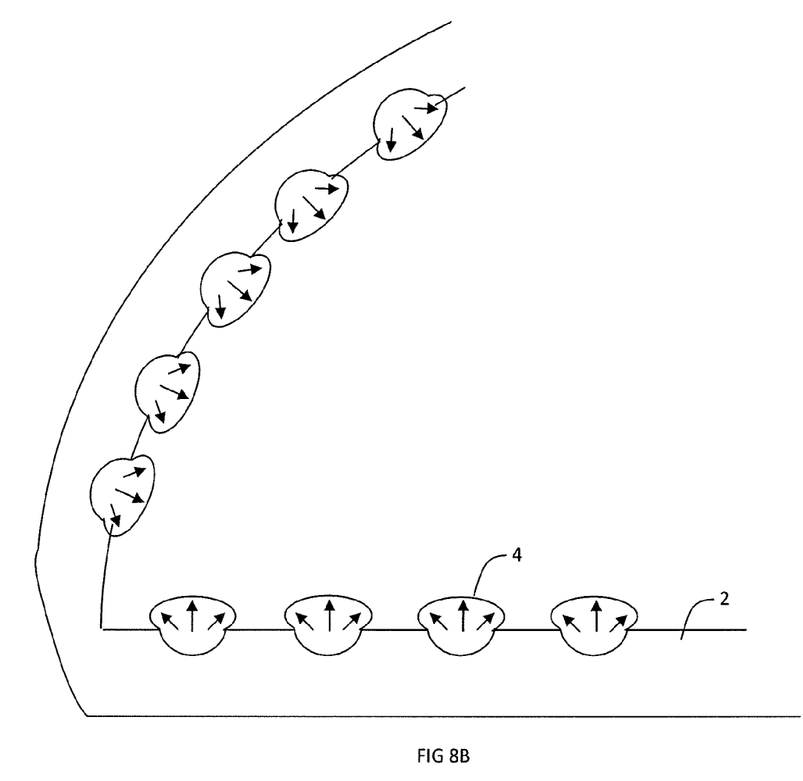

FIGS. 7A through 7B disclose in more detail the insertion of the fluid supplier 13 in the therapeutic port 10. The brachytherapy fluid supplier 13 is intended to provide therapeutic fluid to the breast implant quadrants. Therefore, the brachytherapy fluid supplier 13 is inserted through the input port 10 until reaching a predetermined section. Several procedures may be used to supply the therapy fluid to a particular section. In the present case, the length of the input port is taken into consideration, wherein the brachytherapy fluid supplier 13 is marked to provide visual information of how deep it has been introduced into the input port. The traveled distance of the brachytherapy fluid supplier 13 inside the input port represents the section being reached. FIG. 7A is directed to the insertion process of the brachytherapy fluid supplier 13, which is done perpendicularly (90 degrees) to the input port's surface. As described earlier, both funnel shaped structures, one in the supplier inserter 13a and the other in the input port 10 in the implant, are positioned using ultrasonic guidance and then the brachytherapy dispenser is introduced. FIGS. 8A through 8B represent the expansion of the conducts 4 after the therapy fluid is supplied. The conducts 4 are configured to expand towards the inner surface of the breast implant. This configuration avoids perceiving deformation at the outer surface of the implant, and consequently breast deformation, maintaining a natural appearance. Further, the conduct 4 can be arranged to expand in such way that the whole area is covered by the therapy fluid. After the therapy is performed the therapeutic fluid is removed by a flushing process in order to eliminate the radioactive substance inside the implant 1.

Figure 9:
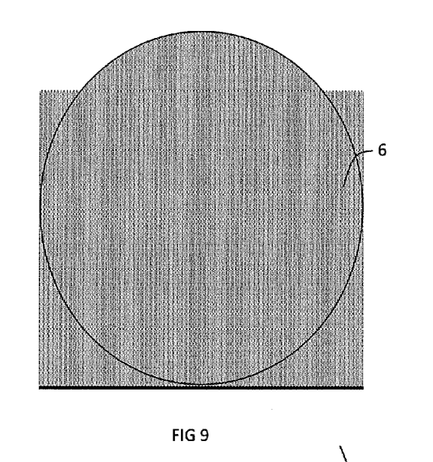
FIG. 9 shows the breast implant with the biodegradable substance mesh in accordance with the principles of the present invention.

FIG. 9 discloses the biodegradable layer 6 covering the breast implant 1. The biodegradable layer 6 controls the foreign body's reaction and therefore minimizes the possibility encapsulation in order to keep a natural feel and appearance. The biodegradable layer covers the first layer of the implant. It can be integrally made with the first layer 2 or added to the surface in the form of mesh or coating. Furthermore, the mesh or coating is provided with drug eluting properties for further treatment to the patient.

Figure 10:
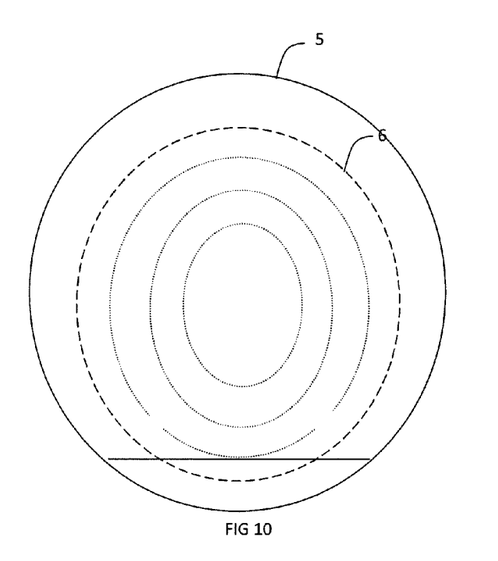
FIG. 10 shows the breast implant with extendable cover in accordance with the principles of the present invention.

FIG. 10 shows the extendable attaching means for the breast implant 1, the third layer of the implant. The attaching means 5 are fixed to the breast implant and may be made of a biodegradable material. The attaching means 5 assists with the fixation and/or fastening of the breast implant 1 and serve as a mesh extension around the implant's border. The third attaching layer can also cover the entire second layer, in this way it will take some time until the body begins the biodegradation process of the drug eluting second layer. This will allow for the wound to heal properly before any chemotherapeutic agent that may affect wound healing is present locally.

Figure 11:
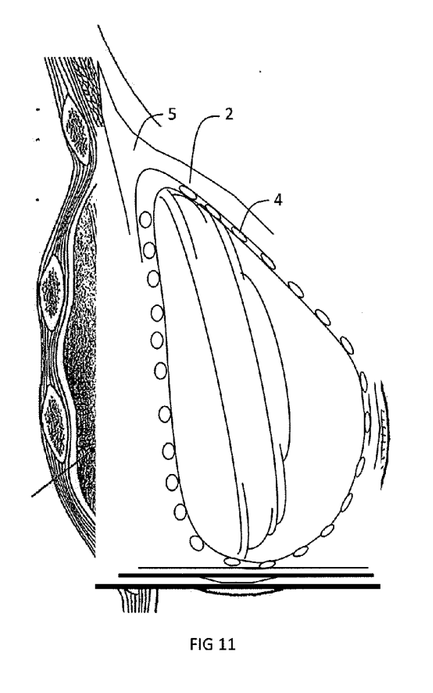
FIG. 11 shows the breast implant positioned inside patient's chest in accordance with the principles of the present invention.

For example, FIG. 11 shows the breast implant in the patient's body. The attaching means 5 assists with the fixation and/or fastening process of the breast implant while the conducts 4 are arranged throughout the first layer 2 in order to provide brachytherapy around the implant 1.

Furthermore, the breast implant 1 is provided with several ports 8, 7, 10. Some ports are directed to the brachytherapy and others are directed to the inflation process of the breast implant 1. In one embodiment, ultrasound guidance is used to perform this procedure. Other guidance methods or procedures may be used alternatively. First, the port for inflation is located substantially at the back part of the breast implant 1.

The location of the port 7 avoids the unpleasant feeling of the port at the outer surface of the patient's skin, and the use of ultrasound guidance results in the use of a smaller port. In the instant case, the material used for the port is easy to recognize by the ultrasound system.

Figure 12:
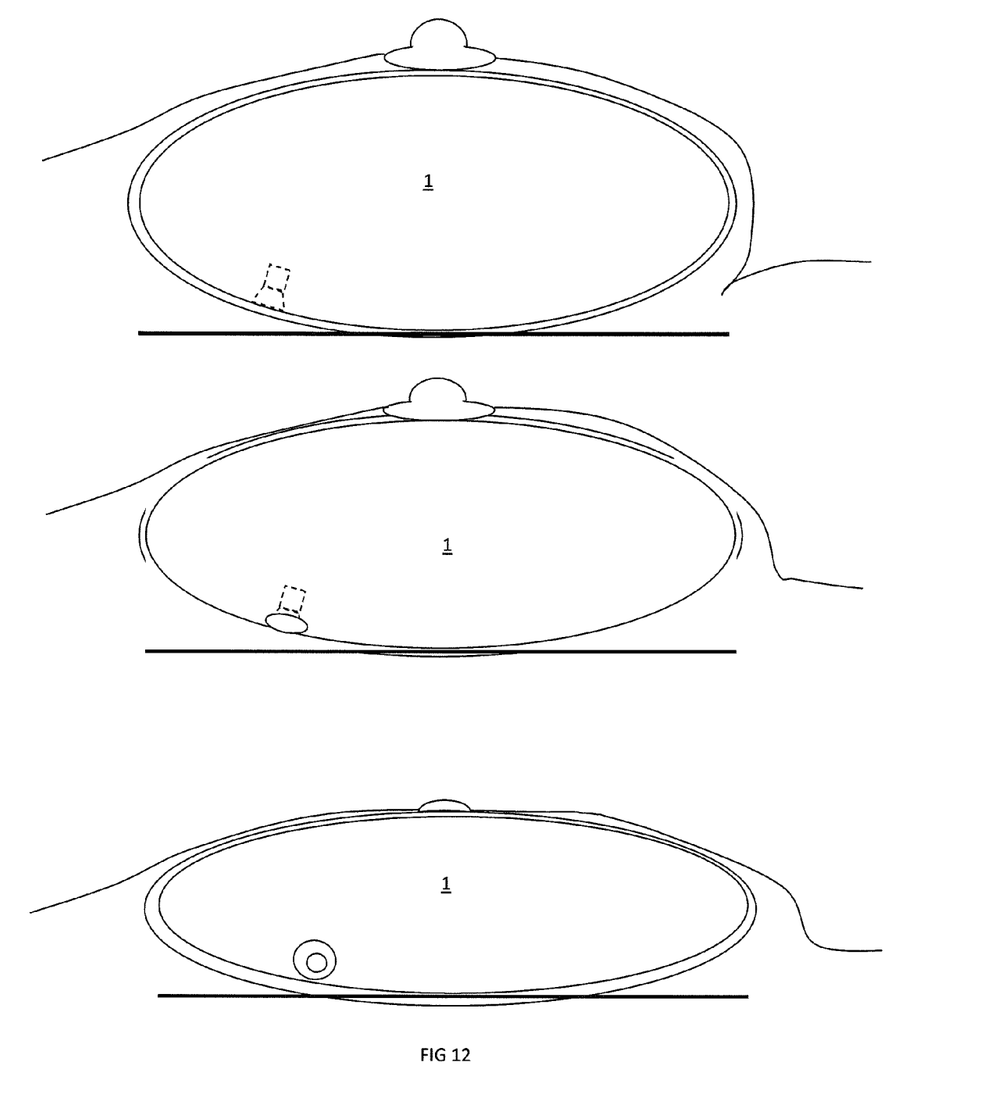
FIG. 12 shows the breast implant's inflation process in accordance with the principles of the present invention.

The location of the port, which is assisted by fixing the breast implant in the proper position using the attaching means 5, is revealed to the physician using the ultrasound system during the inflation process when the patient turns to the side or lateral decubitus position. FIG. 12 shows the process where, after fixing the breast implant 1, the patient is turned to the side in a lateral decubitus position and the breast displacement will result in revealing the port 7, 10.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for therapeutic breast implants. Therefore, the above description should not be taken as limiting the scope of the invention which is defined by the appended claims.

The invention claimed is:

1. An implant, comprising: at least one filling port for the administration of a filling fluid, at least one therapeutic port for the administration of a therapeutic agent, and a closed flexible shell comprising a base portion and a dome-shaped portion defining an internal chamber; and a porous core positioned inside the internal chamber, said porous core having interconnected spaces to allow inflation of the implant with said filling fluid; a first layer having sectioned areas, wherein said first layer comprises a plurality of conducts wherein each conduct is independent from each other, wherein at least one conduct of said plurality of conducts is positioned at one of said sectioned areas in order to administer a therapeutic agent at specific sections of said closed flexible shell; and wherein said therapeutic port comprises an elongated body with a plurality of input ports, each input port being connected to at least one of said plurality of conducts, wherein said plurality of input ports is divided by soft rings to avoid transfer of fluid between sections.

2. An implant as in claim 1, wherein said flexible shell comprises a plurality of layers.

3. An implant as in claim 1, further comprising a second layer made of biodegradable material.

4. An implant as in claim 3, wherein said second layer surrounds the first layer.

5. An implant as in claim 4, wherein said second layer is capable of eluting a chemotherapy drug.

6. An implant as in claim 4, further comprising a third layer.

7. An implant as in claim 2, wherein one of the plurality of layers serves as attachment means.

8. An implant as in claim 7, wherein said plurality of layers comprises a second layer and a third layer, wherein the third layer surrounds the second layer and extends from the second layer away from the first layer, and wherein the third layer serves as the attachment means.

9. An implant as in claim 1, wherein said porous core is made of a malleable cohesive material.

10. An implant as in claim 1, wherein said conducts are arranged around said internal chamber and each conduct covers a pre-determined area of the first layer.

11. An implant as in claim 1, wherein said conducts are arranged to expand towards the chamber and towards an adjacent conduct.

* * * * *